United States Patent
Kohn et al.

(10) Patent No.: US 8,497,513 B2
(45) Date of Patent: Jul. 30, 2013

(54) III-V NITRIDE SEMICONDUCTOR DEVICE COMPRISING A DIAMOND LAYER

(75) Inventors: Erhard Kohn, Ulm (DE); Michele Dipalo, Neu-Ulm (DE); Farid Medjdoub, Goutroux (BE)

(73) Assignee: Universitat Ulm (DE)

( * ) Notice: Subject to any disclaimer, the term of this patent is extended or adjusted under 35 U.S.C. 154(b) by 172 days.

(21) Appl. No.: 12/919,939

(22) PCT Filed: Feb. 26, 2009

(86) PCT No.: PCT/EP2009/001379
§ 371 (c)(1),
(2), (4) Date: Aug. 27, 2010

(87) PCT Pub. No.: WO2009/106328
PCT Pub. Date: Sep. 3, 2009

(65) Prior Publication Data
US 2011/0005942 A1  Jan. 13, 2011

(30) Foreign Application Priority Data
Feb. 28, 2008 (EP) .................................... 08003665

(51) Int. Cl.
*H01L 29/15* (2006.01)
(52) U.S. Cl.
USPC ............. 257/77; 257/192; 257/194; 257/253; 257/E29.249
(58) Field of Classification Search
USPC ...................... 257/77, 192, 194, 253, E29.249
See application file for complete search history.

(56) References Cited

U.S. PATENT DOCUMENTS

| | | | | |
|---|---|---|---|---|
| 7,382,004 | B2 * | 6/2008 | Shur et al. ...................... | 257/253 |
| 8,039,301 | B2 * | 10/2011 | Kub et al. ...................... | 438/105 |
| 8,129,725 | B2 * | 3/2012 | Kunze et al. .................... | 257/76 |
| 2004/0112764 | A1 | 6/2004 | Stokes et al. | |
| 2006/0065912 | A1 | 3/2006 | Beach | |
| 2006/0113545 | A1 | 6/2006 | Weber et al. | |
| 2007/0126026 | A1 | 6/2007 | Ueno et al. | |

FOREIGN PATENT DOCUMENTS

| DE | 102006030305 B3 | 12/2007 |
|---|---|---|
| WO | WO-2007/017252 A1 | 2/2007 |

OTHER PUBLICATIONS

"International Application No. PCT/EP2009/001379, International Search Report and Written Opinion", (Jun. 2, 2009), 13 pgs.

* cited by examiner

*Primary Examiner* — Minh-Loan T Tran
(74) *Attorney, Agent, or Firm* — Schwegman Lundberg & Woessner, P.A.

(57) ABSTRACT

The invention relates to a semiconductor device, in particular to a chemical field effect transistor (ChemFET), a high-electron mobility transistor (HEMT) and an ion-sensitive field effect transistor (ISFET), as well as a method for manufacturing the same. The semiconductor device comprises a structure, the structure comprises a substrate, a first layer comprising GaN and a second layer comprising InAlN, wherein the first and the second layer are arranged parallely to each other on the substrate, and wherein the structure comprises a third layer comprising diamond.

22 Claims, 5 Drawing Sheets

III-V NITRIDE SEMICONDUCTOR DEVICE COMPRISING A DIAMOND LAYER

PRIORITY CLAIM TO RELATED APPLICATIONS

This application is a national stage application under 35 U.S.C. §371 of PCT/EP2009/001379, filed Feb. 26, 2009, and published as WO 2009/106328 A8 on Sep. 3, 2009, which claims priority to European Application No. 08003665.0, filed Feb. 28, 2008, which applications and publication are incorporated herein by reference and made a part hereof in their entirety, and the benefit of priority of each of which is claimed herein.

The invention relates to a semiconductor device, in particular to a chemical field effect transistor (ChemFET), a high-electron mobility transistor (HEMT) and an ion-sensitive field effect transistor (ISFET), as well as a method for manufacturing the same.

ISFETs for application in harsh environments are still a challenge. They lack either an inert, corrosion-resistant and robust electrode or an active FET with characteristics providing high sensitivity. The electrode of choice would be a diamond electrode, the FET of choice a Si-MOSFET or GaN HEMT. Diamond FET structures show very low sensitivity as compared to Si-MOSFETs or AGaN-based HEMTs due to doping problems. Up to now it has not been possible to combine the Si-MOSFET technology with a diamond electrode because diamond with good electrochemical characteristics (no influence from graphitic phases) requires growth parameters incompatible with Si-MOSFETs. State of the art Si-ISFETs normally comprise metal-oxide electrodes (like $TiO_2$), which still show a limited chemical stability.

AlGaN/GaN HEMTs have shown high current densities and channel current modulation efficiencies in electronic (microwave) applications and also in biochemical applications. However, here the use is restricted to a narrow range in pH of the solution around pH neutral and in electrical bias due to electrochemical corrosion. Again, the combination of AlGaN/GaN HEMTs with a high quality diamond electrode has been incompatible up to now in respect to the diamond deposition parameters.

A main problem is that the deposition of polycrystalline diamond with sufficient quality requires growth temperatures above 500° C., preferably between 600° C. and 900° C. In this temperature range, the degradation and the decomposition of GaN and AlGaN/GaN heterostructures becomes a problem.

In the prior art the following ChemFETs are normally applied.

Si-ChemFETs

Si-ISFETs are conventionally fabricated on the basis of Si-MOSFETs. The gate electrode in contact with the liquid is, however, in most cases a metal oxide or metal nitride electrode because of the limited electrochemical stability and corrosion resistance of the $SiO_2$ surface. Therefore, in this case the MOSFET characteristics determine the electrical sensitivity, and the chemical activity of the electrode surface determines the electrochemical sensitivity. Because of the limited stability of the various electrode surfaces, such devices are difficult to use in harsh conditions.

AlGaN/GaN-ChemFETs

AlGaN/GaN heterostructures have been used as ChemFETs in bio-chemical applications in the past. Here the electrochemical activity is caused by surface hydroxyl bonds stemming from the oxygen termination of the surface in the atmosphere. Although the heterostructure is grown under hydrogen-rich conditions and therefore hydrogen terminated, the surface converts quickly due to oxygen termination in the atmosphere. Under anodic polarization the oxidation of the AlGaN barrier material continues and the barrier layer degrades slowly. Thus, the AlGaN/GaN HEMT is only conditionally stable in an electrolyte, its use is thus confined to the rather mild biochemistry.

It therefore can be an object of the present invention to find a semiconductor structure which can be used in a ChemFET which is highly temperature-stable, having excellent electrochemical properties and being highly stable in harsh and hazardous environments.

This object may be solved by the semiconductor device according to claim 1, the method for manufacturing a semiconductor device according to claim 16 and the method for sensing according to claim 23. Advantageous developments of the semiconductor device and the method for manufacturing may be given by the respective dependent claims.

The semiconductor device according to the present invention comprises a structure, the structure having a substrate on which a first layer comprising GaN as well as a second layer comprising InAlN are disposed. The first layer can be in contact with the substrate while the second layer can be arranged directly or indirectly on the first layer. The substrate as well as the first and second layer are preferably flat and are arranged with parallel surfaces above each other. Preferably, the first and the second layer form a InAlN/GaN heterojunction. Such heterojunctions have a high-sheet charge density. FETs with such heterojunctions have a very high output current density of, for example, above 2 A/mm. These heterojunctions are highly temperature-stable up to temperatures of around 1000° C. The InAlN is preferably lattice-matched to the GaN with 17% In.

It is preferred that the semiconductor device further comprises a third layer which comprises diamond. This third layer can be arranged parallely to the first and/or second layer and/or the substrate. It can cover the upper surface of the structure which is the outer surface (faced away from the one adjacent layer) of that layer of the rest of the structure which is most distant to the substrate. It is also possible that the diamond layer only covers this upper surface in regions. Furthermore, the third layer can also cover the entire structure or the side surfaces of the structure.

Depending on the application of the semiconductor device the first layer can be in direct contact with the substrate or the second layer can be in direct contact with the substrate, however it is preferred that the first layer is in direct contact with the substrate.

It is preferred that a barrier (thickness of the InAlN-Layer) of the InAlN/GaN heterostructure has a thickness between 2 nm and 20 nm, preferably of 5 nm. This allows to obtain a high transconductance and a pinch-off voltage accordingly to an electrode electrochemical window if the semiconductor device is a ChemFET.

To obtain an optimum lattice matching between the first and the second layer, the indium content of the second layer is preferably between 0% and 50%, more preferably between 10% and 40%, more preferably approximately 17%.

To obtain a high mobility, the semiconductor device preferably comprises an AlN spacer layer 12 (or smoothing layer) between the first and the second layer. Such a structure, with and without spacer layer 12, shall be referred to InAlN/GaN heterostructure in the following and may contain an AlN spacer 12.

The diamond is preferably single-/poly- and/or nano-crystalline diamond. For high-quality diamond layers this diamond can be disposed on an interlayer for nucleation and insulation.

If the diamond is used for insulation purposes, it can be undoped. However, if the diamond layer should be conductive, it can be n-type doped or p-type doped at least in regions. In particular, the diamond can be doped with boron, preferably with a doping concentration p between $10^{18}$ cm$^{-3} \leq p < 10^{21}$ cm$^{-3}$, preferably $10^{19}$ cm$^{-3} \leq p \leq 10^{20}$ cm$^{-3}$. Such a highly boron-doped diamond film resembles a quasi-metallic electrochemical electrode as used in heavy-duty electrochemical applications. The interface layer of the diamond nucleation should preferably also be conductive and could thus preferably be a carbon-forming metal, doped Silicon, or ideally Ir if single crystal growth is desired. In contrast to a conventional Si-MOS ISFET with metal oxide electrodes, the structure according to the invention can operate in the potentiometric as well as amperometric regime.

To obtain insulation to the semiconductor heterostructure, the single-/poly-/nano-crystalline diamond can be a layered structure of at least two layers, where at least one of these two layers is undoped. It is preferred that the diamond film is nano-diamond with a grain size of 10 nm to 300 nm, preferably between 50 nm and 200 nm, preferably between 100 nm and 150 nm. With such a diamond film the surface can obtain a high electrochemical activity. A layer stack of single crystalline diamond grown on Ir on an InAlN/GaN heterostructure can be covered with an insulating dielectric as for example $SiO_2$.

It is possible to modify the diamond film by specific nanoparticles as for example platinum (Pt) or gold (Au) to enhance specific electrochemical reactions and/or effects.

The semiconductor device can furthermore comprise an interlayer containing at least one metal and/or a carbide-forming metal. The interlayer can furthermore be stoichiometric and/or Si-rich. The interlayer may be deposited by CVD or sputtering or even spin coating from a liquid source.

Thus, the interlayer can comprise amorphous silicon, $Si_3N_4$, $SiO_2$ or other silicon compounds. Titanium and iridium are also possible for the interlayer.

The semiconductor device can have a potential window of water dissociation of approximately or above 3 V in the electrochemical electrode configuration when in direct contact with electrolyte solution.

The semiconductor device can furthermore comprise a passivation layer which can contain intrinsic poly- and/or nano-crystalline diamond. Such a passivation layer can for example be located on the top surface, most distant to the substrate of the structure. In case of a ChemFET such a passivation layer can surround the gate electrode.

The semiconductor device can for example be an ion-sensitive field effect transistor, a high-electron mobility transistor and/or a chemical field effect transistor. In this case the semiconductor structure has a gate. In chemical applications this gate can be in contact with harsh and hazardous chemicals. In this case it is preferred that the third layer, that is the diamond layer, covers this gate contact. Depending on the details of the structure, the third layer can cover only the gate contact or the entire surface having the gate contact. It is also possible that the diamond layer (i.e. the third layer) provides a contact to the gate contact. The gate can furthermore comprise a metal withstanding diamond overgrowth with respect for example to its temperature stability.

To improve the quality of the diamond film, a nucleation layer can be located below this diamond film, for example between a gate contact and this diamond film. Such an interfacial nucleation layer can for example comprise Nickel.

The substrate may for example comprise sapphire, silicon or silicon carbide.

In one embodiment the second layer forms a buffer layer. On its surface the third layer is disposed. On the same surface the third layer is disposed as a MESA. Thereon Ohmic contacts can be arranged. Diamond layer and InAlN layer can be contacted via a Nickel-gate.

According to the invention, the semiconductor device explained above can be produced as follows. First the structure comprising the substrate and the InAlN/GaN heterostructure is produced. Afterwards, MESA etching of the heterostructure can be performed, e.g. parts of the InAlN layer (second layer) are etched away to form InAlN MESAs. The entire InAlN/GaN heterostructure can be etched but only parts of the GaN-buffer on the substrate. Then Ohmic contacts can be deposited and the nano-diamond electrode stack including interlayers can be deposited. Afterwards the diamond and interlayer stack can be etched to access the Ohmic contacts and the gate area. Then the gate contact can be deposited and the electrode can be contacted. Furthermore, a passivation layer can be deposited. To form an interface with a solution to be analyzed, the diamond electrode in the passivation layer can be opened.

The order of the above fabrication steps is specific to the layout of the semiconductor device and may be altered. For example the diamond electrode stack can be grown even before Ohmic contact deposition and after the MESA etching step. Furthermore, the passivation layer can be deposited or sputtered just after the diamond layer stack has been grown. The passivation layer should preferably be chemically inert and a robust material, preferably single-/poly- and/or nano-crystalline diamond or for example a thick polyamide film.

The diamond growth can be performed by virtually all techniques known for the growth of diamond. In particular, hot filament chemical vapor deposition and plasma chemical vapor deposition should be mentioned. For the nucleation on and/or formation of interlayers also bias-enhanced nucleation (BEN) or diamond powder is suitable. In case of bias-enhanced nucleation the material for the interlayer should be conductive. For example, amorphous silicon has been proven to be a suitable and reliable interlayer. It can be deposited by physically enhanced chemical vapor deposition (PECVD) at about 300° C. or by sputtering, whereby the conduction is provided by doping. Alternatively iridium can be sputtered or deposited and will allow a single crystal diamond overgrowth if Ir-deposition results in a oriented surface. It is therefore an ideal nucleation material.

The diamond outgrowth is performed to obtain high-quality material and a stress balance. Typical parameters in a hot filament reactor are: filament temperature between 1900-2200° C., substrate temperature between 300-1000° C., CVD pressure between 0.5-10 kPa. The Poly-/Nano-crystalline diamond can for example have a thickness between severely tenth of nanometers to several micrometers on InAlN/GaN at a temperature in the range of 300° C. to 1000° C. using an amorphous Si-interlayer. The diamond layer may have a pH sensitivity close to the Nernst's limit of 59 mV/pH if the semiconductor device is used as pH-sensor.

The quasi-metallic electrode properties are obtained by p-type boron doping with a concentration of approximately or above $10^{20}$ cm$^{-3}$. Boron can be added to the growth gases in the growth chamber by means of gas, liquid or solid source. Doping concentration in the range of $10^{18}$ to $10^{21}$ cm$^{-3}$ can be achieved for example with a liquid TMB (trimethyl borate) source using a Hydrogen bubbler system, or with the insertion of a boron rod in the CVD chamber. Both techniques are reliable for Hot Filament and for Plasma CVD. Another boron-doping method can be the insertion of diborane gas into the CVD-chamber during the diamond growth. In the case of nanodiamond as used here conductivity can also be obtained by nitrogen doping of the grain boundaries. In this case the conduction is n-type, but the electrochemical stability is limited by the grain boundary properties.

The transconductance and sensitivity are essentially that of the InAlN/GaN HEMT. With a barrier thickness of 10 nm the transconductance can be as high as approx. 300 mS/mm, which is about $10^2$ of that of diamond FETs with boron delta channel and approximately twice of that of AlGaN/GaN FETs.

The above mentioned heterostructure can act as a sensor as well as an electrochemical electrode. The invention provides a chemical sensor which works as an ISFET which is chemically inert and does not corrode due to the diamond cover. If the source and drain contact of such a transistor are not covered with diamond, those areas have to be covered if in contact with aggressive media. Alternatively they can be dimensioned such that they are destroyed after a sufficient lifetime and can be replaced.

The structure according to the invention possesses a wide potential window and therefore allows application under high anodic overpotentials for the detection and oxidation of nearly all organic molecules.

Such a ChemFET structure combines the high corrosion resistance of the diamond electrode for applications in harsh environments with high sensitivity for the first time. The diamond electrode needs to be highly (quasi-metallically) doped to enable amperometric operation.

Depending on the diamond properties (doped and conductive or undoped and insulating) and the interface (seeding with or without interlayer) several device structures can be realized. Due to the high temperature stability of InAlN and the absence of stress in a lattice matched heterostructure, high-quality nanodiamond films can be grown with high quality electrochemical and thermal properties.

The following features are furthermore advantageous for the semiconductor device and the methods according to the invention.

In the Semiconductor device according to the invention the third layer preferably forms an outer layer of the semiconductor device.

The thickness of the second layer is preferably between 2 nm and 20 nm, more preferably between 3 nm and 10 nm and even more preferably 5 nm.

In the semiconductor device according to the invention the third layer preferably comprises single-/poly- and/or nanocrystalline diamond.

In the semiconductor device according to the invention, the diamond and/or the third layer can be doped with boron, preferably with a doping concentration $p<10^{21}$ cm$^{-3}$, preferably $p<10^{20}$ cm$^{-3}$.

The third layer preferably comprises nano-diamond with grains having a size between 10 nm and 300 nm, preferably between 50 nm and 200 nm, preferably between 100 nm and 150 nm at the surface.

In the semiconductor device and the method according to the invention the surface of the third layer is preferably modified by nanoparticles, preferably nanoparticles comprising Pt and/or Au.

If the semiconductor device according to the invention comprises an interlayer comprising at least one metal and/or a carbide-forming metal and/or being stoichiometric and/or being silicon-rich, preferably being located between the second and third layer, the metal of the interlayer is preferably iridium, amorphous silicon, silicon-rich $Si_3N_4$ and/or silicon-rich $SiO_2$ and/or other silicon compounds.

If the semiconductor device according to the invention has a gate contact the gate of the transistor preferably comprises a metal withstanding diamond overgrowth.

In the semiconductor device according to the invention, the interfacial nucleation layer preferably can be deposited on Nickel and/or can comprise Nickel.

The semiconductor device according to the invention can preferably comprises one, two or more Ohmic and/or Schottky contacts, in particular if the device is a transistor as described above.

In the semiconductor device according to the invention the substrate can comprise or consists of Silicon, Sapphire or SiC among others.

In the following advantageous features of the method for manufacturing a semiconductor device are described.

In the method according to the invention a carbon-forming metal interface, preferably comprising W or Ta, can preferably be used to improve diamond nucleation and/or limit diffusion.

After the third layer has been deposited, Ohmic and Schottky contacts can be formed if the device to be produced is a kind of transistor. All transistors mentioned above can be produced in the method according to the invention.

In the method according to the invention the third layer can be being doped, preferably with Boron.

In the method according to the invention at least one layer can be preferably disposed by hot filament chemical vapour deposition, Plasma chemical vapour deposition, in particular microwave assisted plasma deposition, or physically enhanced chemical vapour deposition.

Furthermore, if a layer of the device to be produced should be doped, at least one doping material can preferably added to the growth gas in form of gas, liquid and/or solids.

In the method according to the invention the filament temperature in hot filament deposition is preferably smaller or equal 2600° C., preferably smaller or equal 2400° C., preferably smaller or equal 2300° C., depending on the geometrical layout, if hot filament deposition is applied.

Furthermore, the filament temperature can be greater or equal 2000° C., preferably greater or equal 2100° C., preferably greater or equal 2200° C.

It is preferred that the substrate is held at a temperature smaller or equal 1000° C., preferably smaller or equal 800° C. during the deposition.

If chemical vapour deposition is applied the pressure in the chemical vapour deposition is preferably greater or equal 0.5 kPa, preferably greater or equal 2 kPa, preferably greater or equal 4 kPa.

Furthermore, the pressure in a chemical vapour deposition is preferred smaller or equal 10 kPa, preferably smaller or equal 8 kPa, preferably smaller or equal 6 kPa.

In the following the invention shall be explained with reference to examples.

Figure 1:
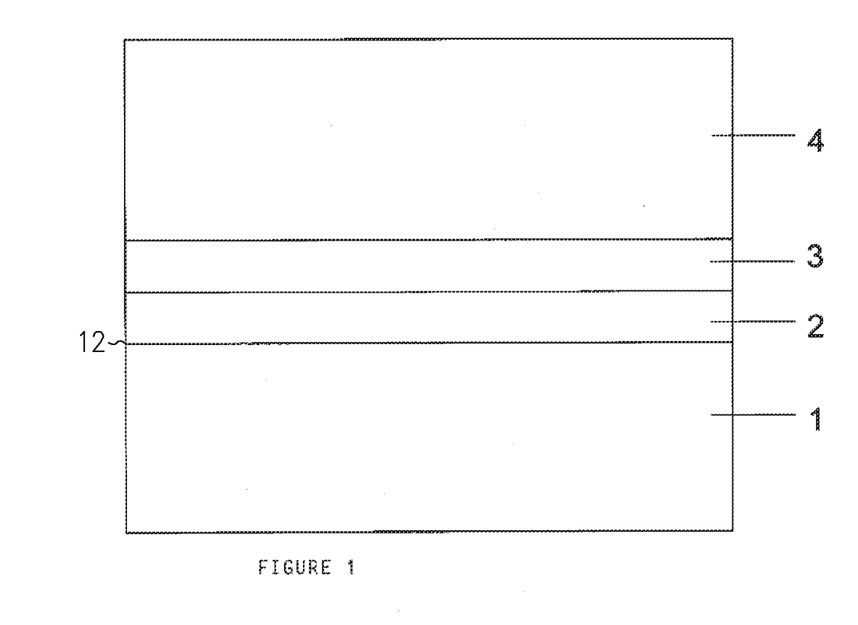
FIG. 1 shows a semiconductor device according to the invention.

FIG. 1 shows the cross-section of a semiconductor device according to the invention. In this example the substrate is not shown. The lowermost layer 1 is a layer comprising GaN (corresponding to the first layer explained above). Adjacent to this on the top a 30 nm thick layer of InAlN is located (corresponding to the second layer explained above). On top of this layer is an amorphous silicon layer as an interlayer having a thickness of 90 nm. On top of this structure a nano-diamond layer is disposed with a thickness of about 400 nm. It has a grain size of about 50 nm.

The amorphous silicon layer has been nucleated with Bios-Enhanced-Nucleation (BEN) directly in the CVD chamber of the Hot Filament system. The BEN and the growth processes are performed in $H_2+CH_4$ atmosphere at the temperature of 750° C., which is possible because of the high thermal stability of InAlN. The InAlN layer morphology did not degrade, neither during the nucleation nor the growth process. First electrical measurements on areas where the diamond film had been removed locally by plasma etching in oxygen show that the 2DEG density is in essence preserved. In FET-like structures the same current levels, which are 100% polarization induced, are identical.

Figure 2:
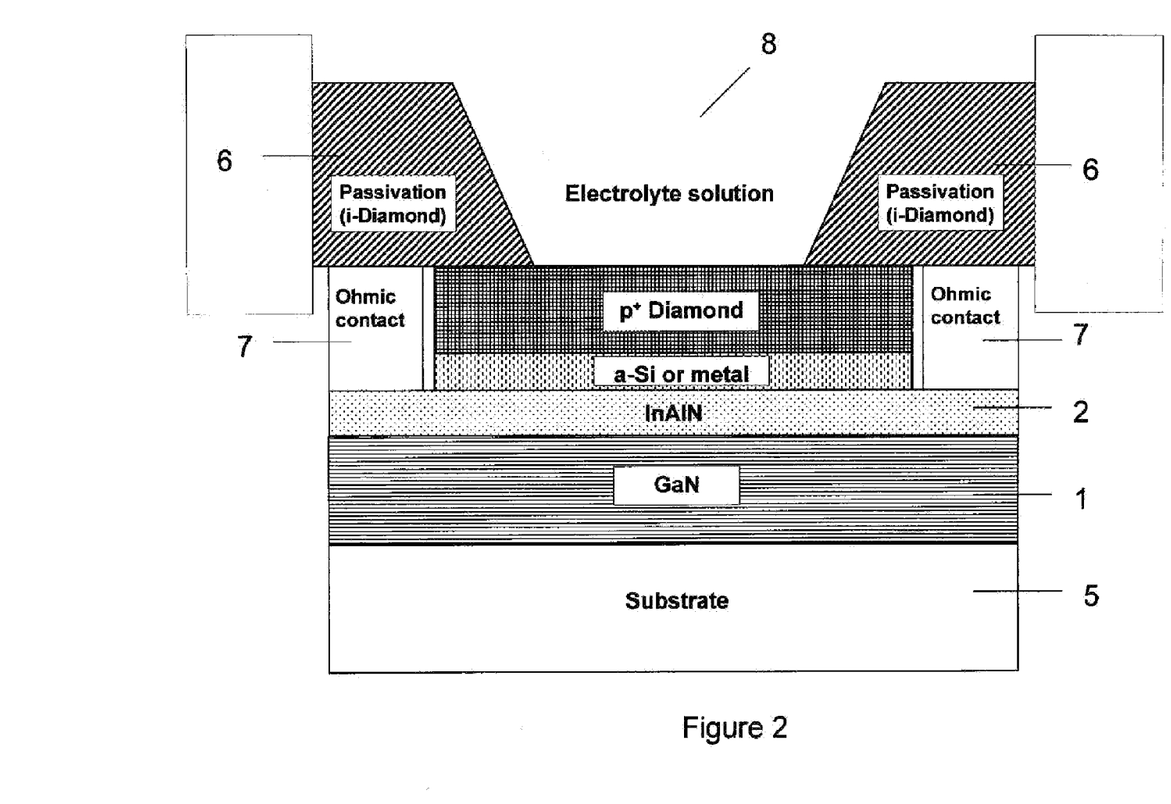
FIG. 2 shows a chemical field effect transistor according to the invention.

FIG. 2 shows a semiconductor device according to the invention which is a chemical field effect transistor. On the flat substrate 5 a GaN layer 1 is located adjacent to the substrate in a parallel plane. On the surface of this layer 1 distant to the substrate 5 an InAlN layer 2 is deposited. The substrate 5 as well as the layers 1 and 2 cover the same area in the mesa area.

On top of the second layer 2 a layer of amorphous silicon or metal 3 is located, on which a $p^+$-doped diamond layer 4 (corresponding to the third layer explained above) is located. Layers 3 and 4 are enclosed or bordered by Ohmic contacts 7. The Ohmic contacts 7 as well as the diamond layer 4 may have the same height and define a common surface. On this surface a diamond layer 6 is located which surrounds an open area 8 through which an electrolyte solution can reach the diamond layer 4. Only the chemically resistant diamond layers are in contact with the electrolyte solution.

Figure 3:
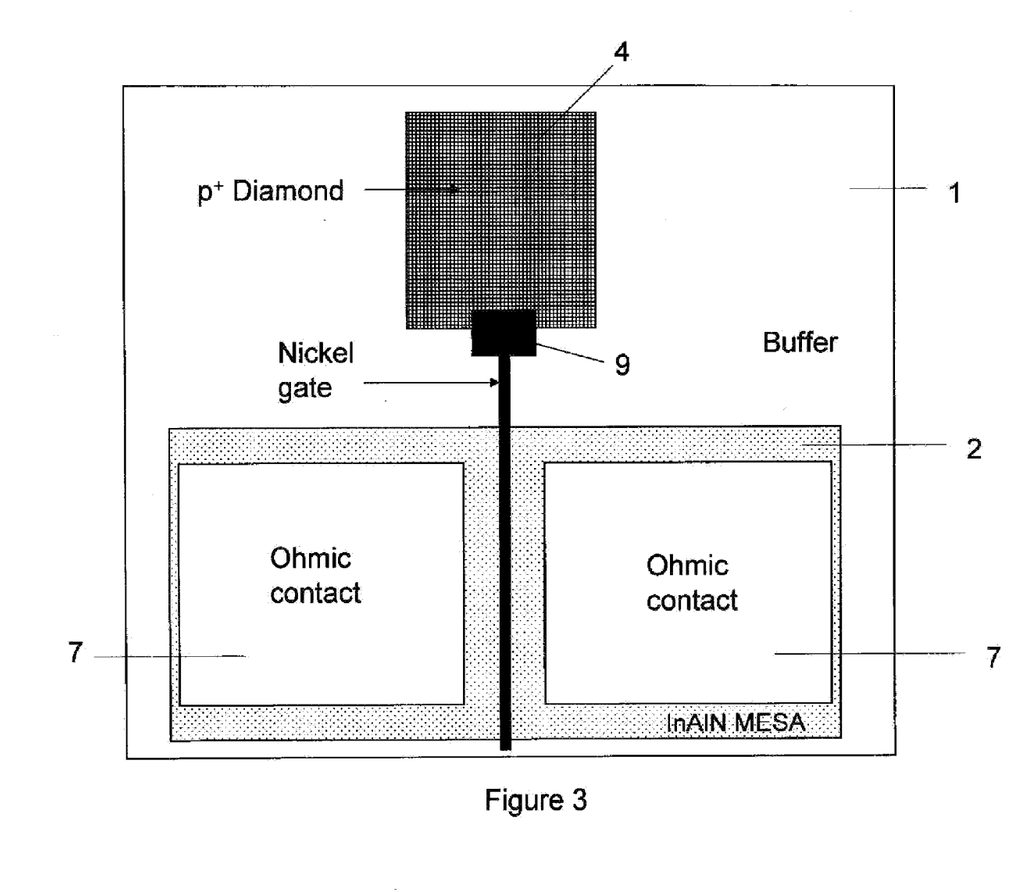
FIG. 3 shows a possible diamond-stacked chemical field effect transistor where the diamond electrode is place outside the FET area.

FIG. 3 shows an alternative chemical field effect resistor according to the invention. Here the diamond electrochemical electrode is placed outside the FET area and outside the MESA area. The diamond layer 4 as well as the InAlN-Layer 2 are located on the Buffer layer 1 (the first layer) in direct contact with these layers. The InAlN layer 2 (second layer) is part of a MESA on which two ohmic contacts 7 are located. The MESA contains the entire InALN/GaN heterostructure etched into the GaN buffer layer. The diamond layer 4 (third layer) does not overlap with the first layer but is rather contacted with the first layer via a Nickel gate contact 9. All contacts, thus also the nickel gate contact 9 may be deposited after diamond deposition. The diamond deposition could also be selective and would not need to cover the MESA 2. The nickel gate contact 9 is partially overlapping the diamond electrode 4 (in a well passivated area) to provide an electrical connection.

Figure 4:
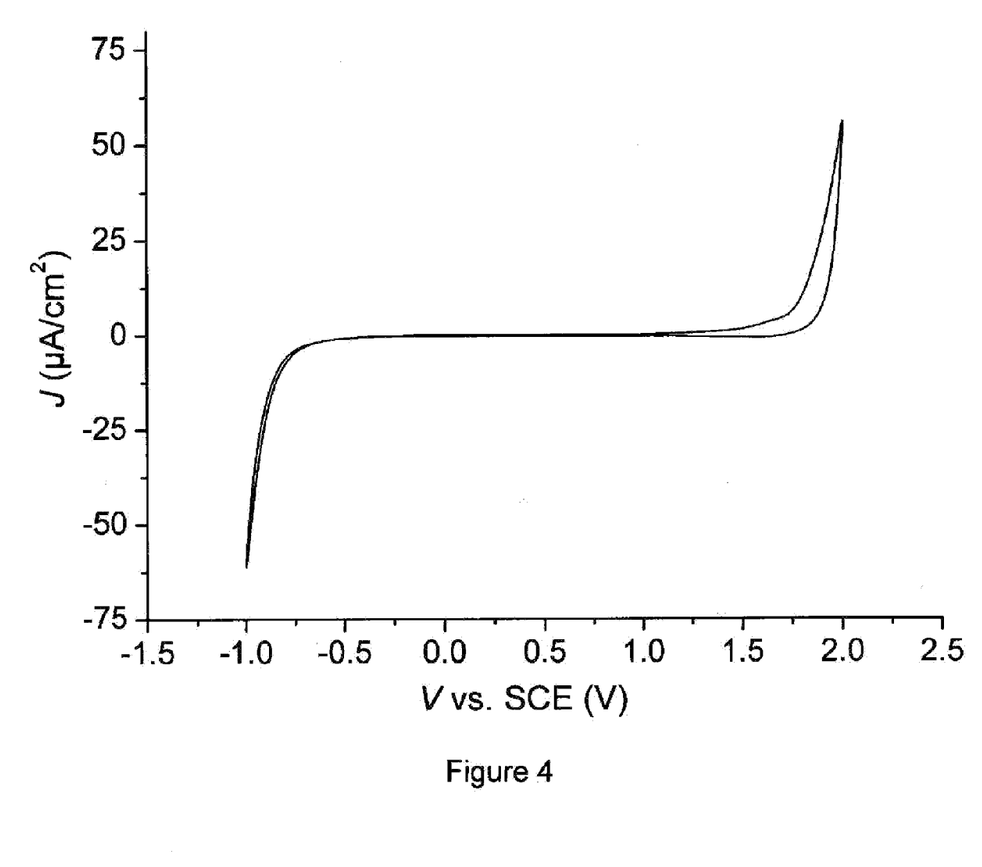
FIG. 4 shows the electrochemical potential window of diamond in water.

FIG. 4 shows the electrochemical potential window of diamond in water. It is the current density J in $\mu A/cm^2$ as a function of the voltage vs. SCE in Volt.

Figure 5:
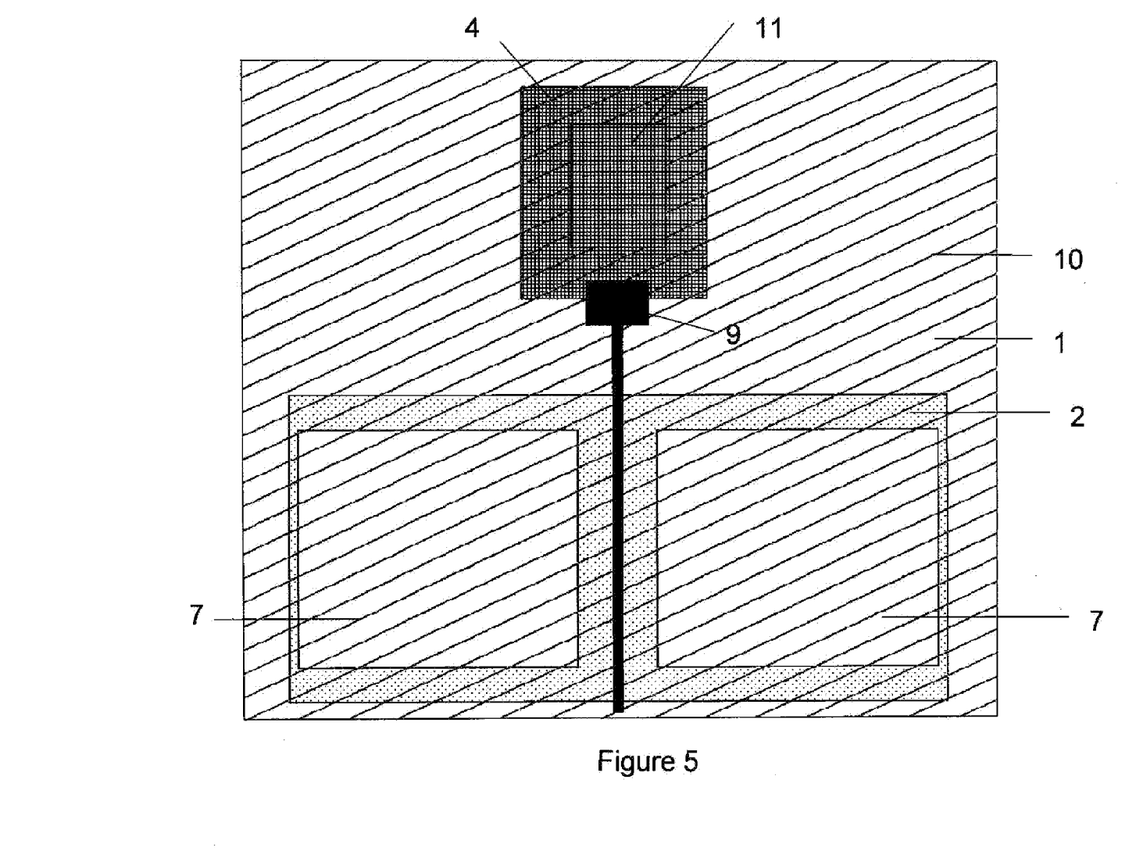
FIG. 5 shows the device of FIG. 3 with passivation and electrode opening exposed to the electrolyte in a possible preferable geometrical arrangement.

FIG. 5 shows the device of FIG. 3 with passivation 10 and electrode opening 11 exposed to the electrolyte in a possible preferable geometrical arrangement. The whole structure is covered by a passivation layer 10 except for a window 11 above the diamond layer 4 which is $p^+$-doped. The diamond 4 below this window 11 is exposed to the electrolyte being analyzed.

What is claimed is:

1. A semiconductor device comprising a structure, the structure comprising a substrate, a first layer comprising GaN and a second layer comprising InAlN, wherein the first and the second layer are arranged parallel to each other on the substrate, and wherein the structure comprises a third layer comprising diamond, wherein the third layer is disposed on an interlayer being adapted to act as a nucleation layer when diamond is disposed on the interlayer and/or being adapted to act as an insulating layer.

2. The semiconductor device according to claim 1, wherein the third layer covers a surface of the structure partially or entirely or covers a surface of the structure most distant to the substrate partially or entirely.

3. The semiconductor device according to claim 1, wherein the first layer is in direct contact with the substrate, and the second layer is arranged on top of the first layer, and the third layer is arranged on top of the second layer.

4. The semiconductor device according to claim 1, wherein the indium content in the second layer is between 0% and 40%.

5. The semiconductor device according to claim 1, comprising a spacer layer including AlN and being located between the first layer and the second layer.

6. The semiconductor device according to claim 1, wherein the third layer is disposed on an interlayer being adapted to act as a nucleation layer when diamond is disposed on the interlayer.

7. The semiconductor device according to claim 1, wherein the diamond and/or the third layer is p-type doped at least in one or more regions.

8. The semiconductor device according to claim 7, wherein the diamond and/or the third layer is doped with boron with a doping concentration $p>10^{18}cm^{-3}$.

9. The semiconductor device according to claim 1, wherein the third layer comprises at least two sub-layers, at least one of which is undoped.

10. The semiconductor device according to claim 1, comprising an interlayer comprising at least one metal, the interlayer being located between the second and third layer.

11. The semiconductor device according to claim 1, providing a potential window of water dissociation of approximately 3 V or more in electrochemical electrode configuration when the third layer comprising diamond is in direct contact with electrolyte solution.

12. The semiconductor device according to claim 1, comprising a passivation layer, being located on a surface of a structure most distant to the substrate and/or on the uppermost surface of the structure and covering this surface at least in one or more regions, the passivation layer comprising intrinsic poly- and/or nano-crystalline diamond.

13. The semiconductor device according to claim 1, wherein the semiconductor device includes at least one of a field effect transistor, a high-electron mobility transistor, or an ion-sensitive field effect transistor.

14. The semiconductor device according to claim 13, wherein the third layer covers only a gate contact or a gate contact pad area of the transistor.

15. The semiconductor device according to claim 13, comprising an interfacial nucleation layer between a gate electrode of the transistor and the third layer.

16. A method for manufacturing a semiconductor device, wherein a structure is produced by disposing a first layer comprising GaN, a second layer comprising InAlN and a third layer comprising diamond, the layers being disposed on each other and/or on a substrate wherein the first and the second layer are arranged parallel to each other on the substrate, and wherein the structure comprises a third layer comprising diamond,wherein the third layer is disposed on an interlayer being adapted to act as a nucleation layer when diamond is disposed on the interlayer and/or being adapted to act as an insulating layer.

17. The method according to claim 16, wherein the first layer is deposited on at least a region of the substrate, the second layer is deposited on at least a region of the first layer, and the third layer is deposited on at least a region of the second layer.

18. The method according to claim 16, wherein an interlayer, a highly doped or undoped single/poly-/nano-crystalline diamond layer, and/or a passivation layer is disposed on at least one of the group comprising the substrate, the first layer and the second layer or between at least two of this group.

19. The method according to claim 16, wherein before the deposition of the third layer diamond nanoparticles are disposed on the layer on which the third layer is to be disposed.

20. The method according to claim 16, wherein the third layer is formed by growing a diamond film on top of the entire surface of the structure or on top of the surface of the structure most distant to the substrate or on the top surface of the structure and that the diamond film is etched back to areas where electrodes are to be located outside the active FET structure.

21. The method according to claim 16, wherein the substrate is held at a temperature greater or equal to 100° C.

22. A method of sensing, wherein a semiconductor device is brought into contact with a chemical solution and a quantity is measured via an electric quantity at the semiconductor device, wherein the semiconductor device comprises a structure, the structure comprising a substrate, a first layer comprising GaN and a second layer comprising InAlN, wherein the first and the second layer are arranged parallel to each other on the substrate, and wherein the structure comprises a third layer comprising diamond wherein the first and the second layer are arranged parallel to each other on the substrate, and wherein the structure comprises a third layer comprising diamond,wherein the third layer is disposed on an interlayer being adapted to act as a nucleation layer when diamond is disposed on the interlayer and/or being adapted to act as an insulating layer.

* * * * *

UNITED STATES PATENT AND TRADEMARK OFFICE
CERTIFICATE OF CORRECTION

PATENT NO. : 8,497,513 B2  
APPLICATION NO. : 12/919939  
DATED : July 30, 2013  
INVENTOR(S) : Kohn et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 171 days.

Signed and Sealed this

Fifteenth Day of September, 2015

Michelle K. Lee
*Director of the United States Patent and Trademark Office*